United States Patent [19]

Strahle

[11] Patent Number: Plant 5,319

[45] Date of Patent: Nov. 6, 1984

[54] ROSE PLANT

[75] Inventor: Glen Strahle, Carlton, Oreg.

[73] Assignee: Carlton Rose Nurseries, Inc., Carlton, Oreg.

[21] Appl. No.: 481,713

[22] Filed: Apr. 4, 1983

[51] Int. Cl.[3] ..... A01H 5/00

[52] U.S. Cl. ..... Plt./20

[58] Field of Search ..... Plt./20

*Primary Examiner*—Bagwill Robert E.

*Attorney, Agent, or Firm*—Chernoff, Vilhauer, McClung, Birdwell & Stenzel

[57] ABSTRACT

A rose plant of the Hybrid Tea Class obtained as a seedling from a seed parent of the Cara Mia variety and a pollen parent of the Volare variety provides classic spiral buds, and long last bright red blooms which maintain their true color from bud through leaf drop, on a continuous basis in a greenhouse.

14 Drawing Figures

BACKGROUND AND SUMMARY OF THE INVENTION

The present invention relates to a new and distinct variety of Hybrid Tea rose plant, a seedling resulting from a definite effort to produce an improvement in this class of rose.

The primary feature of this new variety which connotes its distinctive advance over existing types are its bright red color, its classic spiral bud and its ability to freely yield a quantity of cut flower under greenhouse conditions which maintain true color after being cut, from bud through petal drop.

The variety of rose plant of the present invention was obtained at Carlton, Oreg., as a seedling from a seed parent of the Cara Mia variety (U.S. Plant Pat. No. 3,059) and a pollen parent of the Volare variety (U.S. Plant Pat. No. 4,172). The crossing was made in May 1979, the sowing in February 1980, and the first flower appeared in April 1980.

Asexual reproduction of my new and distinct variety shows that its unique combination of characteristics come true to form and are established and transmitted through succeeding propagations by budding.

BRIEF DESCRIPTION OF THE DRAWINGS

The accompanying photographs show typical specimens of the vegative growth and flowers of the new variety in different stages of development and are depicted in color as nearly true as is reasonably possible to make the same in color illustrations of this character.

FIG. 1 shows a developing flower bud and new growth leaves;

FIG. 2 shows a flower bud as the sepals start to crack;

FIG. 3 shows a nearly open flower bud in the cutting stage;

FIG. 4 shows a full open flower;

FIG. 5 shows flower petals with the inside of the petal above and the outside of the petal below;

FIG. 6 shows the flower with the petals removed exposing the anthers and stamens;

FIG. 7 shows a flower with the petals, stamens, and anthers removed exposing the pistils;

FIG. 8 shows a flower with the petals removed cut in cross-section exposing the receptacle, stamens, and pistils;

FIG. 9 shows a section of the flower stem at the point of branching;

FIG. 10 shows the upper side of a compound leaf;

FIG. 11 shows the lower side of a compound leaf;

FIG. 12 shows a ripe rose hip;

FIG. 13 shows a flowering stem with leaves and flower removed;

FIG. 14 shows a composite of several flowers in different stages of development from nearly open to full flower.

DETAILED DESCRIPTION OF THE DISCLOSURE

The following description was made during December, 1982 of the rose plants of the new and distinct variety growing in a greenhouse at Carlton, Oreg. Color designations are to *The Munsell Limit Color Cascade.*

FLOWER

Flowers borne: Singly on long, normal strength stems.
Quantity of bloom: Abundant in greenhouse.
Continuity: Continuous.
Fragrance: Slight; spicy.
Bud:

*Peduncle.*—Long; medium weight; erect; medium yellowish green; entirely smooth.

*Before calyx breaks.*—Size: medium. Form: long, pointed, with a conspicuous neck; without foliaceous appendages on the surface of the bud; without foliaceous parts extending beyond the tip of the bud.

*As calyx breaks.*—Color: 40-14.

*As first petal opens.*—Size: medium. Form: long, pointed. Color: Outside: 41-13. Inside: 40-13. Opening: It does open up well.

Bloom: Size when fully open: large; 3 inches to 4½ inches.

*Petalage.*—Very double; from 35 to 40 petals; arranged regularly.

*Form.*—Very high centered at first; becoming open high centered; petals remaining at first tightly cupped inward; becoming later at maturity tightly rolled outward.

Petals: Medium thick leathery; with inside velvety; outside satiny.

*Shape.*—Outer: Ovate; with base flat. Intermediate: Obovate; with apex flat. Inner: Obovate; with apex flat.

*Color.*—Color of newly opened flower: Outer petal: Outside surface: 41-14. Inside surface: 40-14. Intermediate petal: Outside surface: 41-13. Inside surface: 40-12. Inner petal: Outside surface: 42-13. Inside surface: 40-11.

*Color of flowers three days after opening.*—Outer petal: Outside surface: 41-13. Inside surface: 40-13. Inner petal: Outside surface: 40-9. Inside surface: 40-10.

*General color effect.*—Newly opened flower: shows both satiny color of outside petals and velvety color of inside petals. Flowers three days open: shows mainly velvety red color, very uniform.

*Behavior.*—Persist.

*Flower longevity.*—Cut roses grown in greenhouse kept at living room temperature 11 days during December.

REPRODUCTIVE ORGANS

Stamens: Many; arranged regularly about pistils.

Filaments: Many; most with anthers; medium length.

*Color.*—24-1.

Anthers: Open at various times; medium size.

*Color.*—29-9. Seldom an anther fused with a pistil.

Pollen: Abundant; gold.

Pistils: Many.

Styles: Uneven; short; medium thickness; loosely bunched.

Stigma: White.

Ovaries: All enclosed in receptacle.

Hips: Medium; globular, smooth; thick fleshy walls; yellow.

Sepals: Permanent; moderately long; spear-shaped; recurved.

Seeds: Many; medium.

PLANT

Foliage:

*Leaves.*—Compound of 5 and 7 leaflets; moderately abundant; medium size; moderately leathery glossy.

*Leaflet.*—Shape: oval with apex acuminate; base obtuse margin simply serrate. Color: Mature upper surface: 20-15. Mature under surface: 20-13. Young upper surface: 23-15. Young under surface: 23-11.

*Rachis.*—Medium. Upper side: smooth grooved. Under side: smooth.

*Stipules.*—Moderately long; very narrow with moderately long points; turning out at an angle of more than 90°.

*Disease.*—Resistance to the average variety growing under the same cultural conditions, subject to mildew.

GROWTH

Habit: Upright; much branched.

Growth: Vigorous.

Canes: Moderately heavy.

Main stems: Dull.

*Color.*—22-13.

*Prickles.*—Several. Color: 29-13. Hairs: None.

*Branches.*—Dull. Color: 22-13 Prickles: Few. Color: 29-14. Hairs: None.

*New Shoots.*—Dull. Color: 23-11. Prickles: Few. Color: 29-11. Hairs: None.

I claim:

1. A new and distinct variety of rose plant of the Hybrid Tea Class obtained as a seedling from a seed parent of the Cara Mia variety and a pollen parent of the Volare variety characterized by its bright red color, its classic spiral bud and its ability to yield large long lasting blooms on a continuous basis in a greenhouse which maintain true color from bud through petal drop, substantially as shown and described.

* * * * *

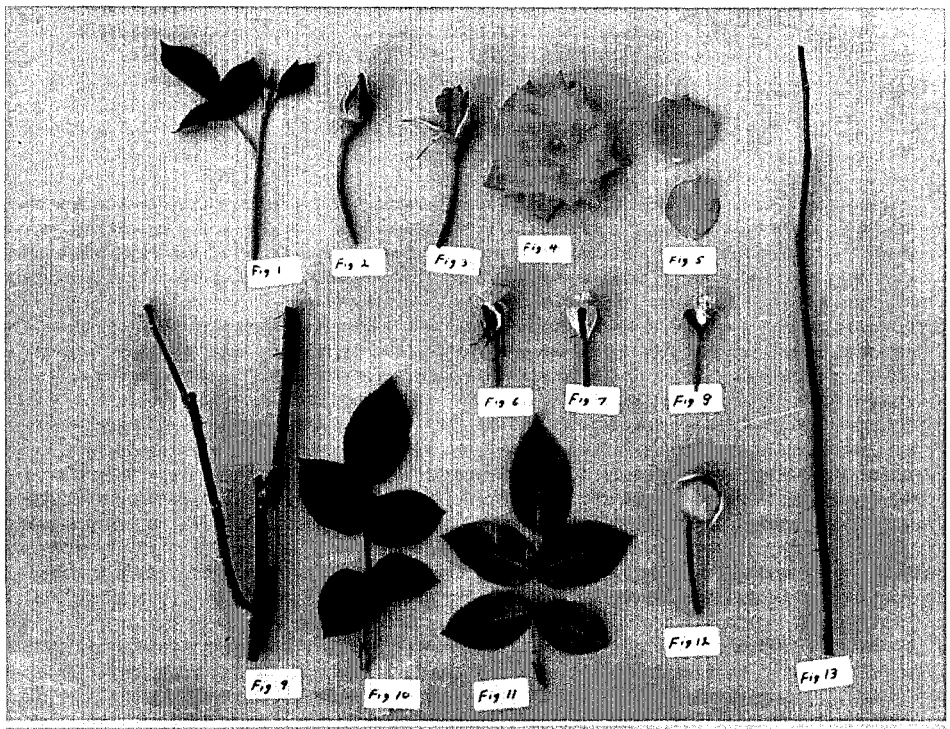
Fig 1
Fig 2
Fig 3
Fig 4
Fig 5
Fig 6
Fig 7
Fig 8
Fig 9
Fig 10
Fig 11
Fig 12
Fig 13
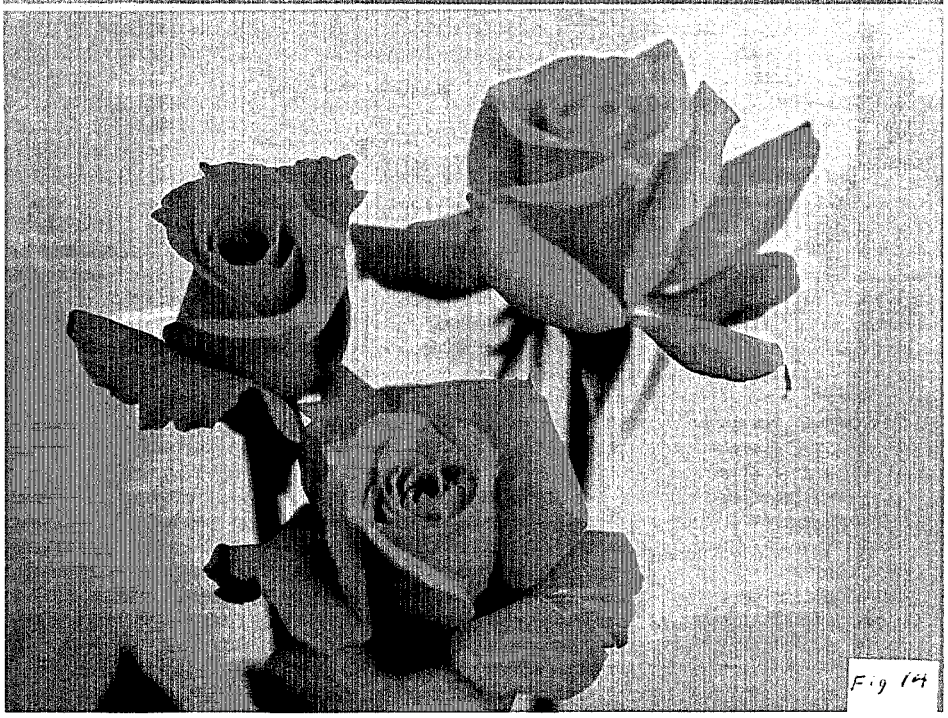
Fig 14

UNITED STATES PATENT AND TRADEMARK OFFICE

CERTIFICATE OF CORRECTION

PATENT NO. : Plant 5,319

DATED : November 6, 1984

INVENTOR(S) : Glen Strahle

It is certified that error appears in the above-identified patent and that said Letters Patent is hereby corrected as shown below:

Col. 2, line 46 Change "ovate" to --obovate--.

Col. 4, line 14 After the word "resistance" insert the word --comparable--.

Signed and Sealed this

*Twenty-ninth* Day of *October 1985*

[SEAL]

*Attest:*

DONALD J. QUIGG

*Attesting Officer*

*Commissioner of Patents and Trademarks—Designate*